(12) United States Patent
Brown

(10) Patent No.: US 8,491,622 B2
(45) Date of Patent: Jul. 23, 2013

(54) MULTI-LAYER INTERNAL NASAL DILATOR WITH TUBULAR EXPANDERS AND COMPOUND DELIVERY PROTRUSIONS

(76) Inventor: Thomas Brown, Kansas City, MO (US)

( * ) Notice: Subject to any disclaimer, the term of this patent is extended or adjusted under 35 U.S.C. 154(b) by 179 days.

(21) Appl. No.: 13/011,023

(22) Filed: Jan. 21, 2011

(65) Prior Publication Data

US 2011/0118775 A1    May 19, 2011

Related U.S. Application Data

(63) Continuation-in-part of application No. 11/438,267, filed on May 22, 2006, now Pat. No. 8,048,102.

(51) Int. Cl.
*A61M 29/00* (2006.01)
(52) U.S. Cl.
USPC .......................................... 606/199

(58) Field of Classification Search
USPC ............................ 606/191, 199; 128/206.11
See application file for complete search history.

(56) References Cited

U.S. PATENT DOCUMENTS

| | | | |
|---|---|---|---|
| 5,882,567 A * | 3/1999 | Cavallaro et al. | 264/255 |
| 2006/0150978 A1* | 7/2006 | Doshi et al. | 128/206.11 |
| 2006/0259064 A1* | 11/2006 | Maryanka | 606/199 |

* cited by examiner

Primary Examiner — Gary Jackson
Assistant Examiner — Eric Blatt
(74) Attorney, Agent, or Firm — Jacob & Associates, LLC

(57) ABSTRACT

An internal nasal dilator and compound delivery apparatus including a holding element and first and second nostril expanders each consisting essentially of a flexible, preferably continuous, and tubular member, wherein at least a portion of the element and expanders are formed of a structural core and compliant outer layer, and/or the apparatus includes a plurality of distending protrusions configured to discharge a quantity of compound over a period.

20 Claims, 8 Drawing Sheets

MULTI-LAYER INTERNAL NASAL DILATOR WITH TUBULAR EXPANDERS AND COMPOUND DELIVERY PROTRUSIONS

CROSS-REFERENCES TO RELATED APPLICATIONS

This U.S. Non-Provisional patent application is a continuation-in-part and claims the benefit of pending U.S. Non-Provisional application Ser. Nos. 11/438,267 filed on May 22, 2006, entitled INTERNAL NASAL DILATOR WITH POROUS COMPOUND DELIVERY MATERIAL, and 11/065,677 filed on Feb. 24, 2005, entitled INTERNAL NASAL DILATOR AND DELIVERY MECHANISM, both of which are incorporated by reference herein.

BACKGROUND OF THE INVENTION

1. Field of the Invention

The present invention relates generally to mechanisms and methods for dilating nasal passages and delivering medication, drugs, or other compounds to a user. More particularly, the present invention concerns an improved internal nasal dilator for increasing nasal breathing efficiency and for delivering a compound within the nostrils of a user, over a period.

2. Discussion of the Prior Art

It is well documented that collapsed or constricted nasal passageways result in a multitude of bodily problems, including sleep apnea, sinus infection, and other respiratory ailments. Another well-known problem associated with reduced passageways is snoring. In this condition, audible sounds produced by the vibration of the soft palate and internal nasal structure can be a nuisance to persons within hearing distance and can affect the quality of sleep of the snoring person. Furthermore, it is also known to be desirous to increase the flow capacity of nasal passageways during exercise, athletics, or otherwise strenuous activity.

To alleviate these problems and better achieve these desires, a variety of nasal dilator mechanisms, including external and internal versions, have been developed over time. Prior art external nasal dilators, typically used during athletic or strenuous activity, often take the form of an adhesive strip that is worn on an exterior portion of the nose and function to lift the walls of the nasal passages. Unfortunately, the frictional grab-strength required by these external dilators often causes discomfort or damage to the skin and soft facial tissues of the user. The external placement required of these dilators exposes them to a variety of forces arising from rubbing against objects, such as pillows, that can prematurely dislodge the dilator.

Prior art internal nasal dilators, on the other hand, function within the nostrils of the user, and as a result are not subject to being prematurely dislodged by external forces. These dilators are typically held in place by a clamping mechanism that pinches the septum generally along two contact points, or by stretching the nostrils enough to result in a compressive force on the dilator sufficient to hold it in place. The non-adjustability of these dilators, however, is problematic given that there are an infinite number of sizes and shapes of human nostrils. The pinching mechanisms of these dilators are also problematic in that they cause discomfort to the user, including pain where prolonged usage is necessary. The fact that some of these internal dilators must stretch the nostrils to a greater extent than is necessary to simply dilate the nostril also causes further discomfort and noticeability.

The prior art also includes nasal dilators combined with gaseous or vapor delivery systems for providing a measured flow of medicine to the user. These combinations, however, typically require that an external source be securely connected to the dilator during usage, which makes them problematically cumbersome. Connection to an external source also reduces comfort by limiting the user to certain positions in order to ensure proper operation, which may further inhibit the user from sleeping. Furthermore, these combinations include notoriously complex mechanical, electrical, or pneumatic parallel clip sections that make their manufacture time-consuming and expensive.

U.S. Pat. No. 6,561,188 to Ellis (Ellis '188), for example, discloses an internal dilator having an internal medicine source. In that arrangement, an anti-histamine layer (27) is not attached to an external source, see FIGS. 8A-8E. The layer (27) is attached to other permeable filter layers and overlays the outlet of the nostrils when in place. However, locating the antihistamine near the outlet of the nostrils reduces the effectiveness of delivery and may be wholly inappropriate for other types of medicines, drugs, or compounds because the proximity to ambient air outside the nose results in a measurable percentage of undelivered medicine. Locating the source up-stream from the mucosal lining within the nasal passageway further diminishes the effectiveness of the combination by preventing the administration of medicine during exhalation. Furthermore, the structure of the disclosed mechanism is so large (relative to the volume of the nasal passages) and complex that it may inhibit airflow during normal breathing and may be prohibitively costly to manufacture.

Thus, due to these and other problems and limitations in the prior art, there remains a long felt need for an improved nasal dilator that dilates the nostrils without substantially restricting the flow of air during respiration, and delivers a desired dosage of compound within the nostrils without extraneous devices or mechanisms.

SUMMARY OF THE INVENTION

The present invention overcomes the problems and limitations in the prior art by providing a yet further improved internal nasal dilator that increases nasal breathing efficiency and delivers a time-released compound within the nostrils of a user, and a method of making the same. As such, the inventive dilator is useful for expanding the nasal passageways and increasing airflow therein. The invention is further useful for more effectively administering a regulated dosage of compound into the passageway of the nose, and for providing increased comfort, in comparison to prior art dilators. Finally, the invention is useful for presenting a novel method of construction.

A first aspect of the invention concerns an internal nasal dilator adapted for use within a nose, wherein the nose defines first and second nostrils separated by a septum defining a local concavity, and each nostril defines in part an internal nasal passageway defining a longitudinal axis, a ridged outlet, and an internal outer wall surface generally opposite the septum. The dilator comprises a holding element configured to contact and apply a holding force to the septum, so as to secure the dilator at least partially within the first and second nostrils when the dilator is donned. The dilator further comprises first and second internal nostril expanders consisting essentially of a flexible, continuous, and tubular nostril engaging member attached to and laterally emanating from the holding element, so as to form a closed loop therewith. The member is upwardly bowed and configured to form generally superjacent layers with the outer wall surface. The holding element and nostril expanders are cooperatively configured to exert an expansive force upon the internal outer wall surfaces, so as to expand the nasal passageways.

A second aspect of the invention concerns the dilator described above, wherein at least a portion of the holding element and nostril expanders are formed of a structural core, and a compliant outer layer fixedly secured relative to the core. A third aspect of the invention concerns the above dilator, wherein the first and second internal nostril expanders each define a plurality of protrusions distending into the passageway, wherein at least a portion of each protrusion is formed at least in part by a compound operable to effect an intended response when inhaled or absorbed by the user.

Other aspects and advantages of the present invention will be apparent from the following detailed description of the preferred embodiments and the accompanying drawing figures.

BRIEF DESCRIPTION OF THE DRAWING FIGURES

A preferred embodiment(s) of the invention is described in detail below with reference to the attached drawing figures of exemplary scale, wherein.

FIGS. 11a-d present a front elevation, side elevation, bottom view, and isometric view, respectively, of a dilator having a plurality of slat protrusions, and a U-shaped clip defining a pinch, in accordance with a preferred embodiment of the invention;

FIGS. 12a-d present a front elevation, side elevation, bottom view, and perspective view, respectively, of a dilator having a plurality of square spike protrusions, and a U-shaped clip defining a pinch, in accordance with a preferred embodiment of the invention; and FIGS. 13a-d present a front elevation, side elevation, bottom view, and perspective view, respectively, of a dilator having a plurality of rounded spike protrusions, and a U-shaped clip defining a pinch, in accordance with a preferred embodiment of the invention.

DETAILED DESCRIPTION OF THE INVENTION

With reference to the figures, an internal nasal dilator and compound delivery apparatus 10 is herein described, shown, and otherwise disclosed in accordance with the preferred embodiments of the present invention. More specifically, the present invention concerns an improved internal nasal dilator 10 that increases nasal breathing efficiency, delivers a compound within the nostrils of a user, and improves comfort when donned (FIGS. 1-13d).

Figure 1:
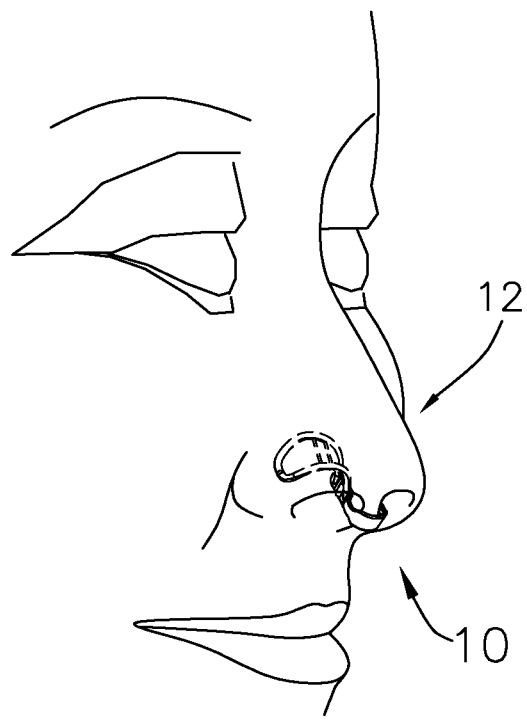
FIG. 1 is a perspective view of a user donning a preferred embodiment of the present invention.
Figure 1A:
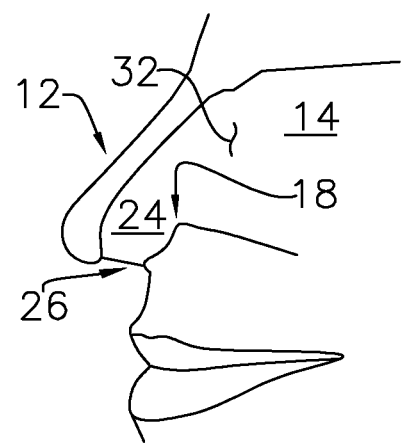
FIG. 1a is an elevation of the inner-anatomy of a nose.
Figure 1B:
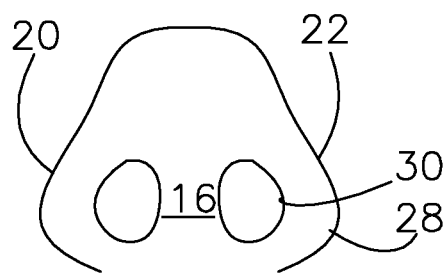
FIG. 1b is a bottom view of the external features of a nose.

The dilator 10 is adapted for use predominately within a nose 12, wherein the term "nose" includes the internal portion 14, consisting of two principal cavities (or "nasal fossae") separated by a vertical septum 16 (FIGS. 1-1b). Each of the nasal cavities fluidly communicates with ambient air conditions through a constricted internal orifice 18 (or "ostium internum"). The nose 12 further includes first and second nostrils 20,22 also separated by the septum 16. Each of the nostrils 20,22 defines in part an internal nasal passageway 24, a ridged nasal outlet 26, and a resistively elastic outer wall (or "ala") 28 having a plurality of microscopic cilia (hairs) emanating therefrom. The internal nasal passageway 24 as used herein, is limited to the vestibules formed by the nose 12, and does not include the nasal cavities and other inner workings of the organ. The passageway distance is defined as the linear distance along the longitudinal axis of the vestibules as measured from the outlet 26 to the orifice 18. The outer wall 28 presents an interior outer wall surface 30 generally opposite the septum 16. Finally, a mucosal lining 32 overlays a significant portion of the nasal passageways 24 and cavities.

As shown in FIGS. 1-13d, the improved dilator 10 includes a holding element 34 configured to contact and apply a holding force to the septum 16, so as to secure the dilator 10 at least partially within the first and second nostrils 20,22, and first and second internal nostril expanders 36,38 (i.e., dilating elements). Each expander 36,38 includes a flexible, preferably continuous, and tubular nostril engaging member 40 that emanates laterally (i.e., traverse the axis of the vestibules) therefrom, so as to form a closed loop therewith. That is to say, in the present invention, the expanders 36,38 are predominately formed by an elongated structural member 40 that is bendingly configured to form a loop or similar geometric shape (FIGS. 2, 6, and 7), such that a region (or "area") is enveloped thereby. As used herein, the term "tubular" shall include hollow, and solid cylindrical geometric shapes or elongated rods having a circular, polygonal, elliptical, or the like cross-section. The member 40 is upwardly bowed and configured to form generally superjacent layers with the outer wall interior surface 30, when the dilator 10 is donned. By defining the enveloped region, the dilator 10 is configured to substantially (greater than 50%) reduce engagement with the interior outer wall surface 30, in comparison to prior art planar structures (e.g., wings, disks, etc.). In a preferred embodiment, the contact surface area of engagement is minimized by utilizing a member 40 having a circular cross-section, so that the member 40 generally engages the outer wall 28 tangentially.

Figure 2:
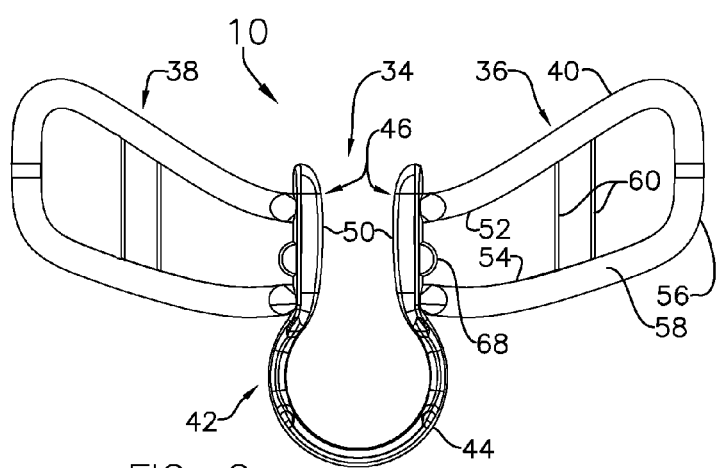
FIG. 2 is a plan view of an internal nasal dilator featuring nasal expanders comprising bowed continuous tubular members and a septum-engaging U-shaped clip, in accordance with a preferred embodiment of the invention.
Figure 4:
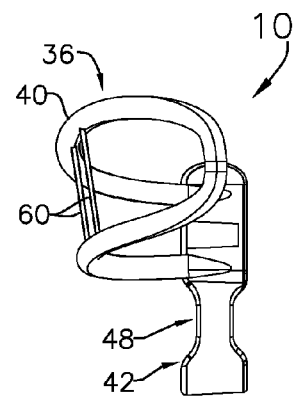
FIG. 4 is a side elevation of the internal nasal dilator shown in FIGS. 2 and 3, particularly illustrating a septum-engaging clip defining upper and lower indentations, in accordance with a preferred embodiment of the invention.
Figure 3:
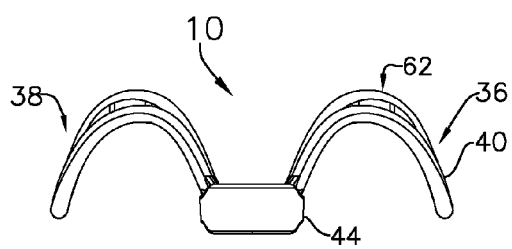
FIG. 3 is a front elevation of the internal nasal dilator shown in FIG. 2, particularly illustrating the bowed configuration of the members.
Figure 6:
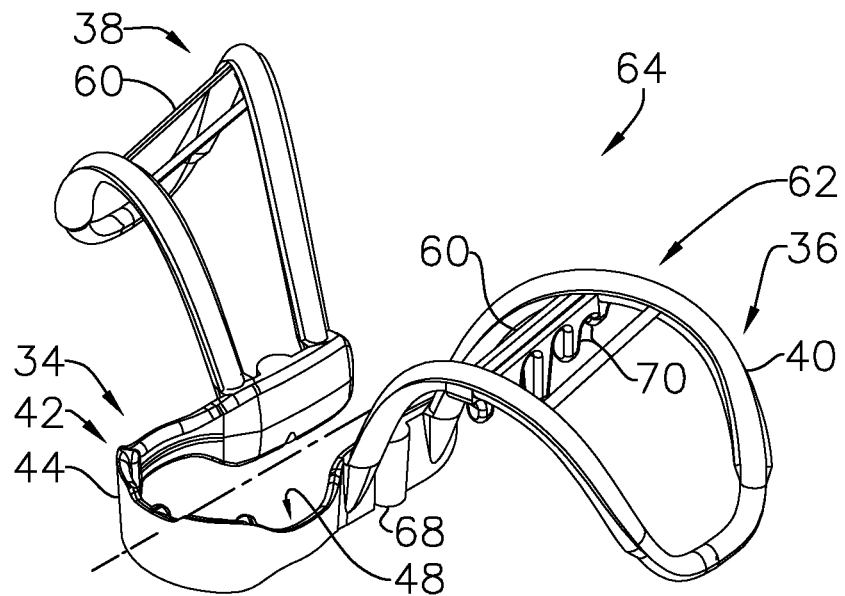
FIG. 6 is an isometric view of the structural core of an internal nasal apparatus, prior to over-molding with a compliant material, in accordance with a preferred embodiment of the invention.
Figure 7:
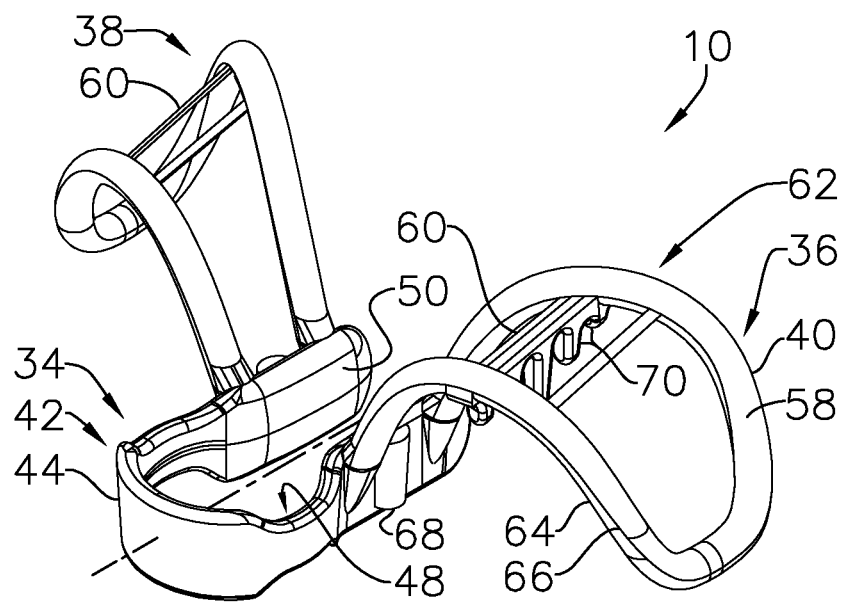
FIG. 7 is an isometric view of the internal nasal apparatus including the structural core shown in FIG. 6, wherein the compliant outer layer has been over-molded to the structural core, in accordance with a preferred embodiment of the invention.
Figure 8:
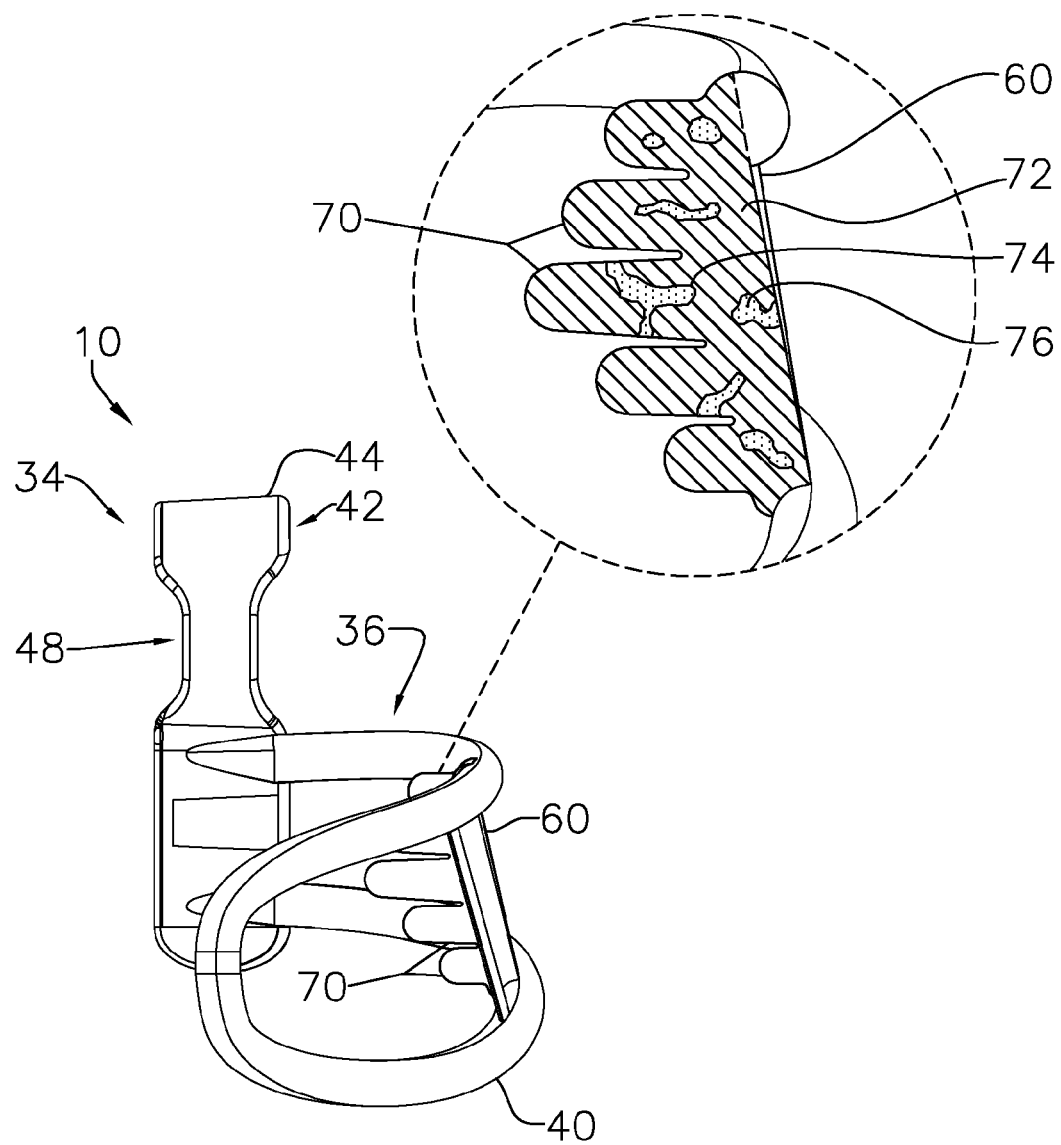
FIG. 8 is an elevation of the internal nasal apparatus shown in FIG. 7, particularly illustrating a plurality of stair-casing protrusions, wherein at least a portion of each protrusion is formed of a compound, in accordance with a preferred embodiment of the invention.

The preferred holding element 34 is a U-shaped septum-engaging clip 42 defining a longitudinal axis (center-line type, FIGS. 6, 7). The clip 42 is formed of a bent middle section 44 defining a first height, as measured orthogonally with respect to the longitudinal axis, and left and right parallel clip sections 46 emanating therefrom and extending generally parallel to the clip axis (FIG. 2). Each parallel clip section 46 defines an indentation 48 (FIG. 4) and a second height generally congruent to the first height. The bent middle section 44 is configured to position the parallel clip sections 46 generally adjacent the septum 16, and the indentations 48 adjacent the ridged outlets 26, when the dilator 10 is donned, so as to provide a comfortable yet snug fit to the user. More preferably, where the element 34 defines upper and lower profiles (FIG. 4) that come into contact with the nostrils 20,22 as the dilator 10 slides up and down the septum 16, upper and lower indentations 48 are preferably defined within the profiles and positioned/configured such that they comfortably receive the ridged outlet 26 when the profiles contact the nostrils 20,22.

In another aspect of the invention, the middle section or first height is larger than, more preferably at least twenty-five, and most preferably, at least fifty percent larger than the parallel sections or second height, so as to increase structural rigidity, reduce the effect of fatigue over time, and thereby increase reusability. The clip 42 may be further configured to facilitate placement and removal by defining an exterior pinch 49 medially within the bent section 44 (FIGS. 11a-13d). Moreover, the pinch 49 may be formed by yet another over-layer external to the over-mold.

The left and right parallel clip sections 46 define generally convex innermost clip surfaces 50 that are configured to engage the local concavity of the septum 16, so that the septum 16 is not pinched by single point sources of contact during usage. The innermost clip surfaces 50 are oriented generally parallel to the septum 16 in the normal position (FIG. 2). More preferably, each of the surfaces 50 presents a surface area not less than 0.2 square centimeters, and most preferably, not less than 0.5 square centimeters. Finally, so as not to damage the mucosal lining 32 during placement and removal, the preferred innermost clip surfaces 50 present a gradually contoured shape. It is believed that this improved design significantly increases comfort to the user, while stimulating the trigeminal nerve and dilating the nasal passage.

More particularly, each tubular member 40 is formed by first and second legs (or leg sections) 52,54 emanating from the holding element 34, and a bent portion 56 interconnecting the legs 52,54. As previously mentioned, the closed loop defines an enveloped region or enclosed area that is bridged by the two legs 52,54. The legs 52,54 are preferably oppositely bowed or divergent, so as to increase the enclosed area, thereby further dilating the passageway 24 along the longitudinal axis. Through observation of at least one sampling, it is appreciated that in this configuration, the instant dilator 10 increases airflow through the passageway 24 during normal breathing by approximately 30 percent, while minimizing engagement with the microscopic cilia of the internal outer wall 28.

To increase structural rigidity, each nostril expander 36,38 preferably includes at least one, and more preferably, a plurality of cross beams 60 interconnecting the legs 52,54 of the loop. More preferably, where the continuous member 40 presents a vertical crest 62 (FIG. 3), the cross-beams 60 are attached to the continuous member 40 at the crest, so as to generally bifurcate the closed loop. Where the cross beams 60 and member 40 define first and second cross-sectional areas, respectively, and the first area is substantially less than the second area. The cross beams 60 preferably interest the legs 52,54 interiorly within their height, and more preferably medially, so as to minimally constrict airflow in the passageway 24.

Figure 5:
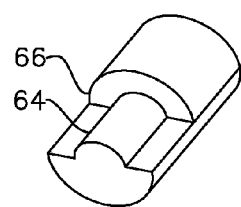
FIG. 5 is a segmental view of a nasal dilator comprising a structural core and compliant outer layer, in accordance with a preferred embodiment of the invention.

In another aspect of the invention, at least a portion of the dilator 10 is preferably formed of a structural core 64, and a compliant outer layer 66 fixedly secured to the core 64. The compliant layer 66 preferably defines the contact area of engagement 58 (FIGS. 5-7). In a preferred embodiment, the expanders 36,38 and holding element 34 are entirely formed of the core 64 and outer layer 66. More preferably, only an upper sector (e.g., the upper half) of the member 40 along the legs 52,54 and the entire bent portion 56 are formed by the core 64 and layer 66 (FIGS. 6, and 7). Moreover, in a preferred embodiment the entire interior surface of the septum engaging clip 42 along the parallel clip sections 46, and the entire bent middle section 44 are formed by a core 64 and compliant layer 66. The core 64 is configured to provide rigidity throughout the dilator 10 while the outer layer 66 is configured to provide comfort to the user during insertion and removal, and along the contact surface area of engagement 58, when the dilator 10 is donned.

The dilator 10 in this configuration may be formed by a dual molding process, wherein the core 64 is first produced, then inserted in a second mold or die (not shown) and is over-molded with the compliant material. Alternative means for forming the compliant outer layer 66 include dipping at least a portion of the core 64 in a soft pre-set material. In a preferred embodiment, the outer layer 66 may comprise of a compressible soft foam, such as a urethane foam approximately 0.025 centimeters thick. To facilitate an over-molding construction, the core 64 preferably defines at least one rib 68 operable to tangentially engage the second mold and space a remainder portion of the core 64 therefrom, so as to allow the over-mold resin to flow around the core 64. The rib(s) 68 serve to properly locate the core 64 within the second mold and facilitates ejection. Preferably the left and right parallel clip sections 46 and the interior surface of the bend middle section 44 of the core 64 of the U-shaped clip 42 each present at least one rib 68 (FIG. 6).

It is appreciated by those of ordinary skill in the art that the core 64 and outer layer 66 preferably present chemical compositions having a common base molecule, such as propylene, to promote bonding therebetween. Other suitable compositions include any non-toxic, hypoallergenic, natural or synthetic polymers, with high elastomeric properties (e.g., a low Young's modulus and high yield strain). As used herein, the terms "compound" and "composition" shall not be given their strict definitions in chemistry, but shall include elements, emulsions, suspensions, mixtures and other forms or combinations of substance suitable for use with the present invention. In a preferred embodiment, the selected composition and configuration of the holding element 34 and nasal expanders 36,38 may be configured to result in an inelastically bendable and therefore permanently conformable dilator 10 that is able to generally retain the shape of the nostrils 20,22 and septum 16.

In operation, after selecting a dilator 10 of suitable size for the user, the dilator 10 is installed by gently bending the expanders 36,38 inward and slightly opening the U-shaped clip 42 to increase the distance between the innermost clip surfaces 50. The expanders 36,38, and left and right parallel clip sections 46, are then inserted through the outlets 26 of the nostrils 20,22 and released. The dilator 10 is slid further into the nostrils 20,22 and adjusted as necessary to reach the desired final location. More preferably, the dilator 10 is maneuvered into place such that the vertex of the bent section 44 is adjacent the exposed portion of the septum 16 (FIG. 1). Once in place, the dilator 10 exerts holding and dilating forces upon the nose 12 as it attempts to revert to its normal uncompressed condition shown in FIGS. 2-13d. More particularly, the expanders 36,38 apply outward biasing forces to the outer walls 28 to maintain the nostrils 20,22 in the open position shown in FIG. 1, and the left and right parallel clip sections 46 compress the septum 16 to help breathing and treat a plurality of adverse conditions (e.g., snoring, etc.).

Yet another aspect of the present invention concerns a nasal apparatus 10 having an improved compound (e.g., medicant) delivery system, wherein each expander 36,38 includes a plurality of protrusions 70 distending into the nasal passageway 24, as variously shown in the exemplary embodiments of FIGS. 6-13d. Each protrusion 70 may be formed of a porous material 72 defining a plurality of interstitial openings 74 (FIG. 8) or present a homogenous structure. The apparatus 10 further includes a quantity of a compound 76 embedded or impregnated into the material 72, and operable to effect an intended response when inhaled or absorbed by the user. Alternatively, the compound 76 may be coated onto a non-reactive core formed by the material, for example, in a similar manner to the core 64 and over layer 66 previously described. Here, the coating preferably presents a film thickness between zero and 1.5 millimeters, more preferably between 0.5 and 1.3 millimeters, and most preferably 1.27 millimeters (0.05 inches).

More particularly, where each nostril expander 36,38 includes a cross beam 60 attached to the member 40, preferably at the crest 62, the protrusions 70 distend from the cross beam 60, as shown in FIGS. 6-13d. Where each passageway 24 defines a longitudinal axis, the protrusions 70 are preferably collimated, so as to generally define a straight line parallel with the axis. This, it is appreciated, minimizes obstruction within the passageway 24. As shown in FIGS. 11a-13d, the protrusions 70 may define various geometric shapes, pluralities, arrays, and configurations. For example, a plurality of longitudinally aligned slats (FIGS. 11a-d), a plurality of square spikes (FIGS. 12a-d), or a plurality of rounded spikes (FIGS. 13a-d) may be collimated and presented as shown.

Figure 9:
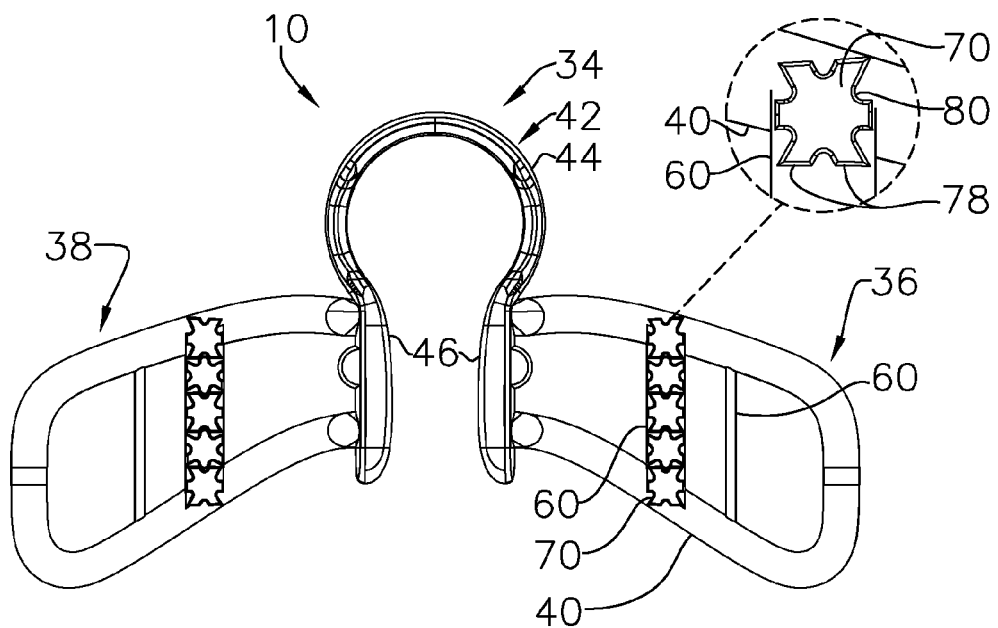
FIG. 9 is a plan view of an internal nasal apparatus, particularly illustrating a plurality of protrusions defining, in enlarged caption view, a plurality of radial projections and recesses, in accordance with a preferred embodiment of the invention.
Figure 10:
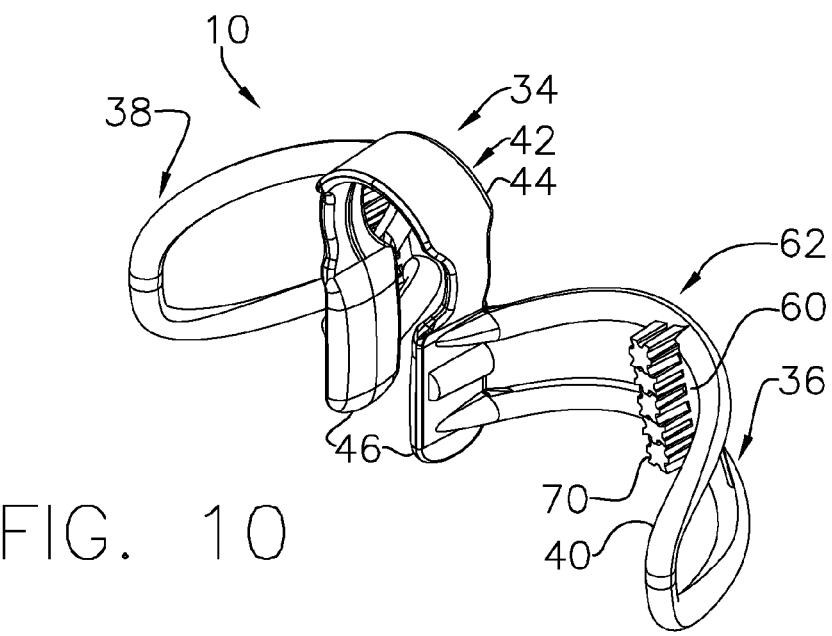
FIG. 10 is a perspective view of the internal nasal apparatus shown in FIG. 9.
Figure 11B:
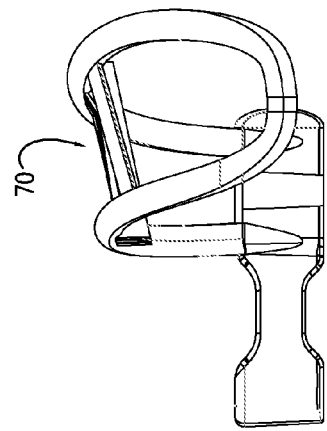
Figure 11D:
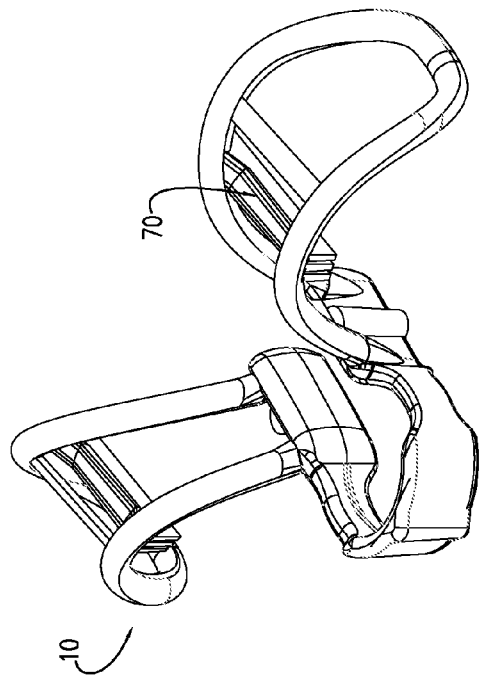
Figure 11A:
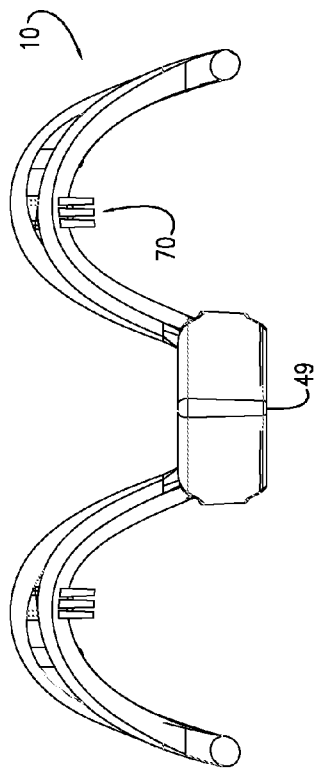
Figure 11C:
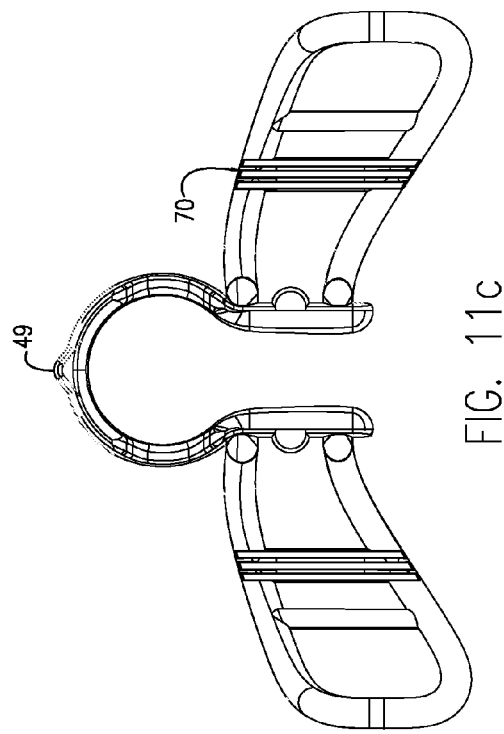
Figure 12A:
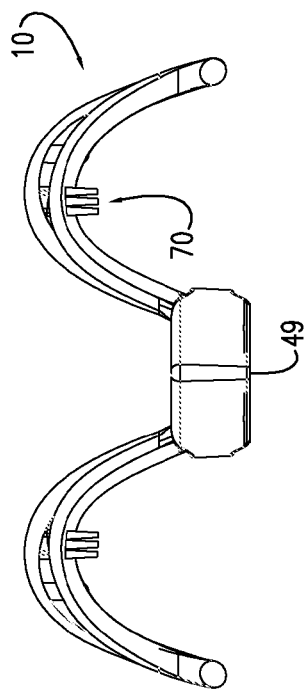
Figure 12B:
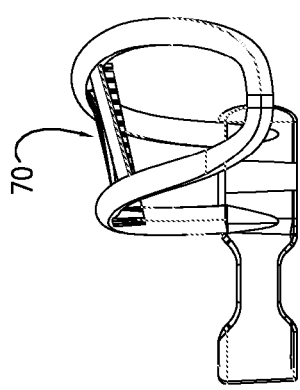
Figure 12C:
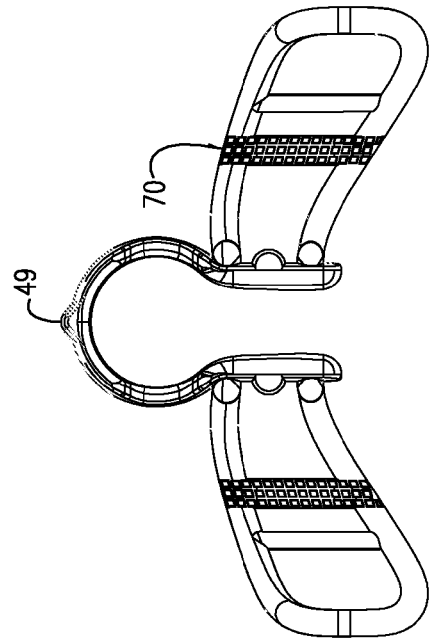
Figure 12D:
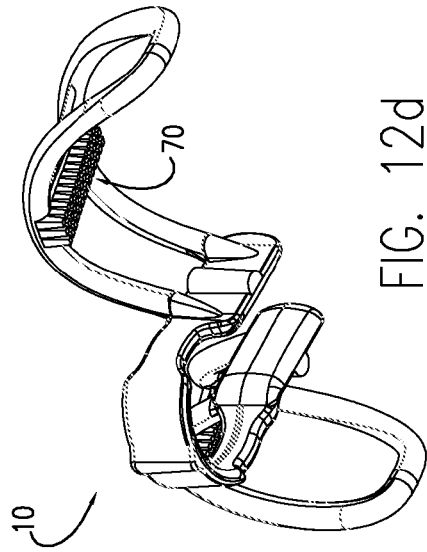
Figure 13A:
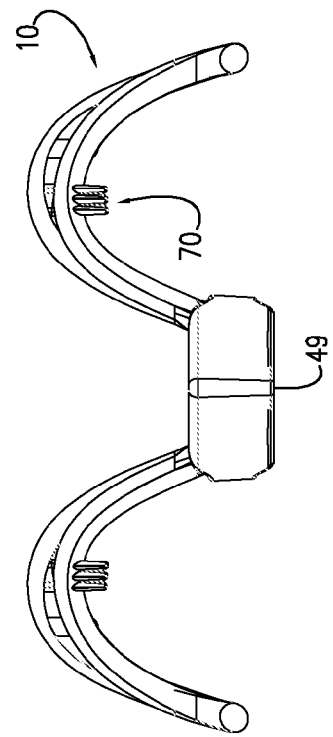
Figure 13B:
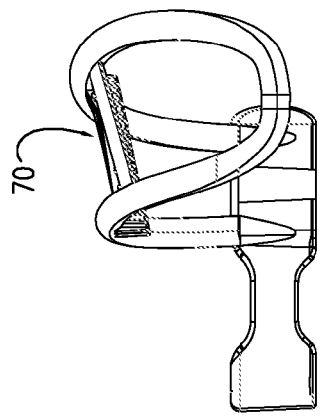
Figure 13C:
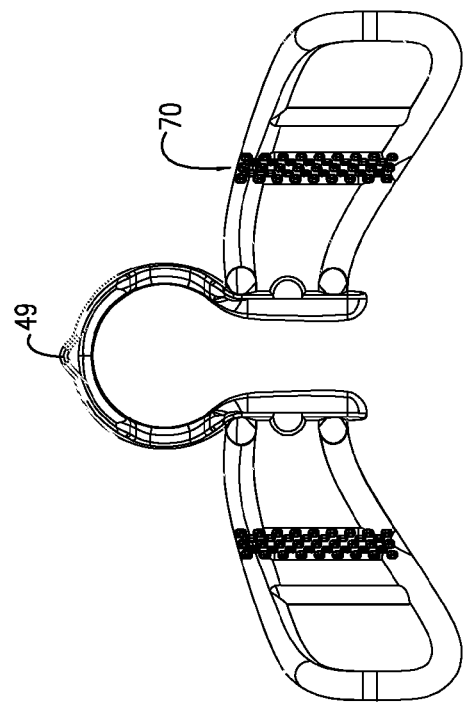
Figure 13D:
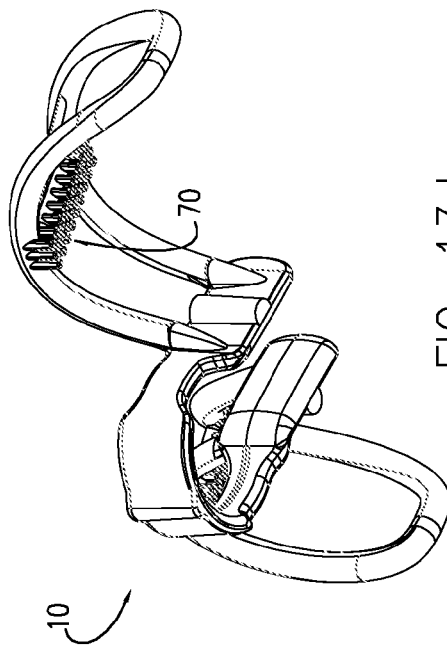

In a preferred embodiment, the protrusions 70 present distally decreasing lengths (FIGS. 6-8), so as to present a cascading or staircase configuration. This configuration increases the exposure of each protrusion 70 to airflow within the passageway 24 when the user inhales or exhales, thereby promoting the transfer of compound 76 into the passageway 24 via evaporation and capillary effect. Here, the distal protrusions 70 are the shortest, which also reduces the likelihood of coming in contact with and irritating the septum 16 or interior outer wall surface 30. The lengths of the protrusions 70 may vary, however, for most human applications it is appreciated that a length between 1 and 6 millimeters is sufficient to effect the intended function of the invention. In a preferred embodiment, the protrusions 70 are configured to increase the surface area exposed to airflow, and as such may present a cross-section defining a plurality of radial projections 78 and/or recesses 80 (FIGS. 9 and 10).

It will be appreciated that the compound 76 may be medicinal or non-medicinal in nature, and may include therapeutic or aromatic substances. For example, the compound 76 may comprise any one or combination of conventional nasal delivery agents, including ionic zinc, pain relief agents, antihistamines/decongestants, scenting agents, herbal supplements, insulin, growth hormones, asthma drug medication, germicides, microbicidal agents, and other beneficial agents. In most cases, the compound 76 preferably further includes ethylene-vinyl acetate, so as to more facilely cure, and be embedded or impregnated into the core material 72.

The apparatus 10 is configured to discharge the compound 76 in the form of airborne particulates from the protrusions 70 and into the passageway 24 over a period, so that they could be carried to the lungs and/or absorbed directly into the bloodstream. More preferably, the compound 76 is discharged over a period of at least one hour, and, most preferably, over a period within the range of four to twelve hours. In this regard, the preferred apparatus 10 is ideally designed to carry a time-released paste having sufficient viscosity, or a sublimating solid at nasal temperatures, to effect gradual discharge. It will be appreciated by those of ordinary skill in the art that gradually discharging the compound 76 increases the efficiency of absorption into the blood stream, and, therefore, the effectiveness of the active ingredient(s).

More particularly, the preferred compound carrying material 72 presents porosity and adhesion characteristics to enable a high filler acceptance rate. The material 72 and compound 76 are cooperatively configured so as to release a desired dosage of compound 76 over a period (e.g. 10 to 15 ml/cm$^2$/hr). An exemplary material 72 presenting the necessary flexural capacity, adhesion characteristics, and porosity is an ethylene-vinyl acetate (EVA) copolymer of suitable vinyl acetate gradation. It is appreciated that the level of vinyl acetate included determines characteristics of the copolymer including, but not limited to, the porosity, crystallinity, flexibility, and rigidity of the copolymer, as well as its resistance to salt, water, and other environments. More particularly, a preferred material 72 for use with the present invention is an EVA copolymer containing, but not limited to, a vinyl acetate constituency within the range of 25% to 35%. For example, a 33% vinyl acetate and 73 shore A durometer, or a 28% vinyl acetate and 80 shore A durometer EVA copolymer, may be utilized. One such suitable brand of EVA is Elvax®, made and manufactured by the Dupont corporation, of Wilmington, Del. It is further appreciated that the vinyl acetate gradation may be modified, so as to increase the porosity of the material 72, and that an increase in porosity results in a larger deliverable dosage, but does not affect the period of delivery. Ethylene butyl resins are also suitable for use with the present invention. Finally, it is also within the ambit of the invention to utilize other material configured to produce a suitable continuous open-cell structure.

The preferred forms of the present invention and modes of operation described above are to be considered illustrative only, and should not be utilized in a limiting sense in interpreting the scope of the present invention. Obvious modifications to the exemplary embodiments, as set forth above, could be readily made by those skilled in the relevant arts without departing from the spirit of the present invention or the contemplated scope of protection. The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An internal nasal dilator adapted for use within a nose, wherein the nose defines first and second nostrils separated by a septum, and each nostril defines in part an internal nasal passageway having a longitudinal axis, a ridged outlet, and an internal wall surface generally opposite the septum, said dilator comprising:

a holding element configured to contact and apply a holding force to the septum so as to secure the dilator at least partially within the first and second nostrils when the dilator is donned; and first and second internal nostril expanders each consisting essentially of a bent tubular member attached to and laterally emanating away from the holding element and cooperatively forming a closed loop with the holding element, wherein each member is curved to form generally superjacent layers with the internal wall surface of the nose when the dilator is donned, wherein the closed loop is oriented such that when the dilator is donned, a line can be drawn intersecting a first point on the closed loop and a second point on the closed loop, the second point being generally opposite the first point on the closed loop, wherein said line is generally parallel to the longitudinal axis of the nasal passageway; and wherein the holding element and nostril expanders are cooperative configured to exert an expansive force upon the internal wall surfaces, so as to expand the nasal passageways.

2. The dilator as claimed in claim 1, wherein the holding element defines first and second indentations, and the element is configured such that the indentations are adjacent the outlets, when the dilator is donned.

3. The dilator as claimed in claim 1, wherein the holding element includes a U-shaped septum-engaging clip having a bent middle section defining a first width, and left and right parallel clip sections emanating therefrom and defining a second width, and the first width is larger than the second width, so as to increase structural rigidity.

4. The dilator as claimed in claim 1, wherein the continuous members and nostrils define a contact surface area of engagement, and the members present circular cross sections, so as to minimize the contact surface area of engagement.

5. The dilator as claimed in claim 1, wherein the continuous members include first and second legs emanating from the holding element, and a bent portion interconnecting the legs, the closed loop defines an enclosed area, and the legs are oppositely bowed, so as to increase the enclosed area.

6. The dilator as claimed in claim 1, wherein the nostril expanders present a structural rigidity, and further include at least one longitudinally oriented cross beam configured to increase the structural rigidity.

7. The dilator as claimed in claim 6, wherein the continuous member presents a vertical crest, and said at least one cross beam is attached to the continuous member at the crest.

8. The dilator as claimed in claim 6, wherein said at least one cross beam and continuous member define first and second cross-sectional areas, respectively, and the first area is substantially less than the second area.

9. The dilator as claimed in claim 8, wherein the continuous members and nostrils define a contact surface area of engagement, and said at least one cross beam presents a circular cross-section and/or is spaced from the nostril, so as to minimize the area of engagement.

10. An internal nasal dilator adapted for use within a nose, wherein the nose defines first and second nostrils separated by a septum, and each nostril defines in part an internal nasal passageway, a ridged outlet, and an internal wall surface generally opposite the septum, said dilator comprising:

a holding element presenting a first contact surface area of engagement and configured to contact and apply a holding force to the nose, so as to secure the dilator at least partially within the first and second nostrils when the dilator is donned; and first and second internal nostril expanders presenting a second contact surface area of engagement, attached to the holding element, and each configured to exert an outward force upon the interior outer wall surface, so as to cause the respective nasal passageway to expand, when the dilator is donned, each of said first and second internal nostril expanders cooperatively defining a closed loop with at least a portion of the holding element, wherein the closed loop is oriented such that when the dilator is donned, a line can be drawn intersecting a first point on the closed loop and a second point on the closed loop, the second point being generally opposite the first point on the closed loop, wherein said line is generally parallel to a longitudinal axis of the nasal passageway; and wherein at least a portion of the holding element and nostril expanders are formed of a structural core, and a compliant outer layer fixedly secured relative to the core, such that the layer defines the first and second areas of engagement.

11. The dilator as claimed in claim 10, wherein the expanders and holding element are generally entirely formed of the core and layer.

12. The dilator as claimed in claim 10, wherein the core and layer are constructed during a molding process where the core is placed within a mold, and the core defines at least one rib operable to tangentially engage and space a remainder portion from the mold.

13. The dilator as claimed in claim 10, wherein the core and outer layer are formed of a common base molecule, so as to promote bonding therebetween.

14. The dilator as claimed in claim 13, wherein the base molecule is propylene.

15. An internal nasal apparatus adapted for use within a nose of a user, wherein the nose defines first and second nostrils separated by a septum, and each nostril defines in part an internal nasal passageway, a ridged outlet, and an internal wall surface generally opposite the septum, said apparatus comprising:

a holding element configured to apply a holding force to the nose, so as to secure the apparatus at least partially within the first and second nostrils when the apparatus is donned; and first and second internal nostril expanders each consisting essentially of a continuous tubular member emanating from and forming a closed loop with the holding element, and defining a plurality of protrusions that are configured to distend into the passageway away from the internal wall surface of the nose when the dilator is donned, wherein each closed loop is oriented such that when the dilator is donned, a line can be drawn intersecting a first point on the closed loop and a second point on the closed loop, the second point being generally opposite the first point on the closed loop, wherein said line is generally parallel to a longitudinal axis of the nasal passageway; and wherein at least a portion of each protrusion includes a quantity of compound operable to effect an intended response when inhaled or absorbed by the user over a predetermined period.

16. The apparatus as claimed in claim 15, wherein the nostril expanders further include a cross beam attached to the member, and the protrusions distend from the crossbeam.

17. The apparatus as claimed in claim 15, wherein the protrusions each present a cross section defining a plurality of radial projections and/or recesses, so as to increase the surface area of the protrusion.

18. The apparatus as claimed in claim 15, wherein each passageway defines a longitudinal axis, the protrusions are collimated, so as to generally define a straight line, and the line is generally parallel with the axis, so as to minimize obstruction in the passageway.

19. The apparatus as claimed in claim 18, wherein the protrusions present distally decreasing lengths.

20. The apparatus as claimed in claim 15, wherein the compound further comprises ethylene-vinyl acetate.

\* \* \* \* \*